(12) United States Patent
Kladakis et al.

(10) Patent No.: US 8,394,121 B2
(45) Date of Patent: Mar. 12, 2013

(54) INTRACARDIAC IMPLANT FOR DELIVERY OF ALARMINS AND METHODS THEREOF

(75) Inventors: Stephanie M. Kladakis, Stoneham, MA (US); Robert L. Cafferata, Santa Rosa, CA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 854 days.

(21) Appl. No.: 12/352,281

(22) Filed: Jan. 12, 2009

(65) Prior Publication Data

US 2009/0182372 A1    Jul. 16, 2009

Related U.S. Application Data

(60) Provisional application No. 61/034,993, filed on Mar. 9, 2008, provisional application No. 61/034,642, filed on Mar. 7, 2008, provisional application No. 61/010,871, filed on Jan. 11, 2008.

(51) Int. Cl.
*A61B 17/08* (2006.01)

(52) U.S. Cl. ........................................ 606/213; 606/200

(58) Field of Classification Search .................. 606/139, 606/151, 157, 213, 215
See application file for complete search history.

(56) References Cited

U.S. PATENT DOCUMENTS

| | | | | |
|---|---|---|---|---|
| 5,653,970 A | * | 8/1997 | Vermeer | 424/70.24 |
| 5,853,422 A | * | 12/1998 | Huebsch et al. | 606/213 |
| 2008/0249562 A1 | * | 10/2008 | Cahill | 606/215 |

OTHER PUBLICATIONS

Bruhn, B. W. and Mueller, B. W. Proceed. Intern. Symp. Control. Rel. Bioact. Mater. 18:668-69 (1991).
Conti, B. et al., "Use of polylactic acid for the preparation of microparticulate drug delivery systems," J. Microencapsulation, 9:153-166 (1992).
Koosha, F. Ph. D. Dissertation, 1989, Univ. Nottingham, UK., Diss. Abstr. Int. B 51:1206 (1990).
Mathiowitz, E. and Langer, R. "Polyanhydride microspheres as drug delivery systems," M. Donbrow Ed., in "Microcapsules Nanopart. Med. Pharm." CRC, Boca Raton, Fla., 1992, Ch. 5, pp. 99-123.
Ogawa, Y. et al., "A new technique to efficiently entrap leuprolide acetate into microcapsules of polylactic acid or copoly(lactic/glycolic) acid," Chem. Pharm. Bull., 36:1095-103 (1988).
Shi, Y., J.E. Evans, and K.L. Rock, "Molecular identification of a danger signal that alerts the immune system to dying cells", Nature, 2003. 425(6957): p. 516-21.

* cited by examiner

*Primary Examiner* — Corrine M McDermott
*Assistant Examiner* — Gregory Anderson
(74) *Attorney, Agent, or Firm* — DLA Piper LLP (US)

(57) ABSTRACT

The invention provides a cardiovascular occluder for treating a cardiovascular abnormality comprising a frame and an alarmin or an alarmin activator bound to the surface of the frame. The invention further provides methods of manufacturing the cardiovascular occluder and methods of treating cardiovascular abnormalities by delivering the cardiovascular occluder.

23 Claims, 1 Drawing Sheet

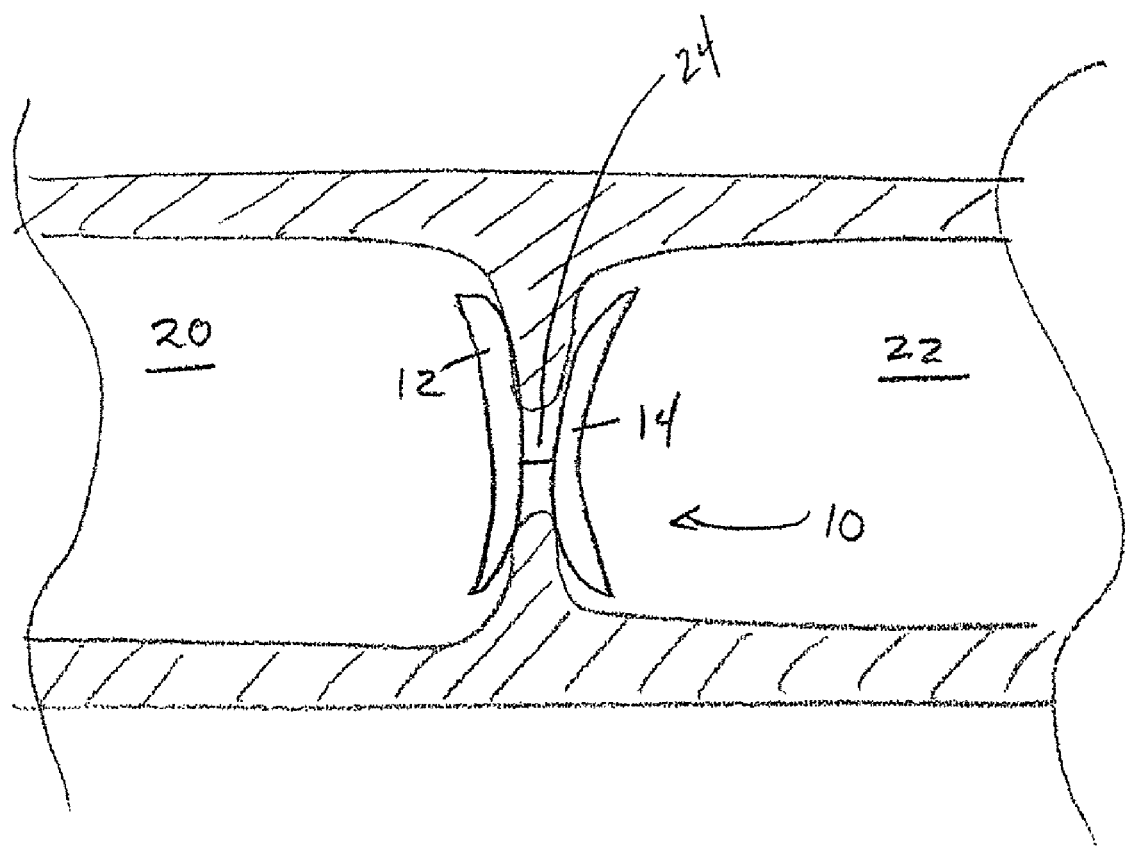

INTRACARDIAC IMPLANT FOR DELIVERY OF ALARMINS AND METHODS THEREOF

CROSS-REFERENCE TO RELATED APPLICATIONS

This application claims the benefit under 35 U.S.C. 119(e) of U.S. Provisional Patent Application No. 61/010,871, filed on Jan. 11, 2008, entitled "Intracardiac Implant For Delivery Of Uric Acid And Uric Acid Precursors And Methods Thereof", which is hereby incorporated by reference herein in its entirety; U.S. Provisional Patent Application No. 61/034,642, filed on Mar. 7, 2008, entitled "Intracardiac Implant For Delivery Of Alarmins And Methods Thereof", which is hereby incorporated by reference herein in its entirety and U.S. Provisional Patent Application No. 61/034,993, filed on Mar. 9, 2008, entitled "Methods For Manufacturing Intracardiac Occluders Incorporating Alarmins And Alarmin Activators", which is hereby incorporated by reference herein in its entirety.

BACKGROUND OF THE INVENTION

Congenital intracardiac defects such as atrial septal defects, ventricular septal defects, and patent foramen ovale (PFO), a type of atrial septal defect, are well recognized intracardiac abnormalities in mammals. A PFO, for example, is a persistent, one-way, usually flap-like opening in the wall between the right atrium and left atrium of the heart. Since left atrial (LA) pressure is normally higher than right atrial (RA) pressure, the flap typically stays closed. Under certain conditions, however, RA pressure can exceed LA pressure, creating the possibility for right to left shunting of blood, permitting blood clots to enter the systemic circulation. In utero, the foramen ovale serves as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two overlapping layers of tissue: the septum primum and septum secundum. However, autopsy studies have shown that a probe-detected patent foramen ovale (PFO) persists in up to approximately 25% of adults. Using contrast echocardiography (TEE), a patent foramen ovale can also be detected in approximately 25% of adults. These PFOs are congenital and are not typically the result of trauma, inflammation, ischemia or other underlying pathology associated with tissue injury. In effect, these defects are not the result of or surrounded by acutely injured tissue as would be found at the site of an acute myocardial infarct.

Studies have confirmed a strong association between the presence of a PFO and the risk for paradoxical embolism or stroke. Although the cause of ischemic stroke is not known, in approximately 40% of cases paradoxical embolism via a PFO is considered in the diagnosis, especially in young patients. In addition, there is evidence that patients with PFO and paradoxical embolism are at increased risk for future, recurrent cerebrovascular events.

Although the presence of a PFO has no therapeutic consequence in an otherwise healthy adult, patients suffering a stroke or transient ischemic attack (TIA) in the presence of a PFO and without another identifiable cause of the ischemic stroke are considered for prophylactic therapy to reduce the risk of a recurrent embolic event. These patients are commonly treated with oral anticoagulants, which have potential adverse side effects, such as hemorrhaging, hematoma, and interactions with a variety of other drugs. In certain cases, such as when anticoagulation is contraindicated, surgery may be used to close a PFO. Suturing a PFO closed typically requires attachment of the septum secundum to the septum primum with either continuous or interrupted sutures under direct visualization for example, by a thoracotomy, or via port access surgery.

Nonsurgical closure of PFOs and other congenital intracardiac defects have become possible with the advent of implantable umbrella closure devices and a variety of other similar mechanical closure designs, developed initially for percutaneous closure of atrial septal defects (ASD). These devices allow patients to avoid the potential side effects often associated with anticoagulation therapies. However, currently available designs of septal closure devices present drawbacks, such as high complication rates and residual leaks. In addition, since many septal closure devices were originally designed to close ASDs, which are true holes, rather than the flap-like anatomy of most PFOs, many closure devices lack the anatomic conformability to effectively close a PFO.

A need exists for a septal closure device or occluder that can provide complete closure of an intracardiac defect in a minimum amount of time, that has a lower complication rate, and that is simple and inexpensive to use and manufacture.

Alarmins are intracellular endogenous molecules that react to triggering events, including the presence of pathogens, misfolded or modified proteins, genomic alterations or exposed hydrophobic portions of molecules, by activating intracellular cascades that lead to a healing response. Alarmins, when released into the body's circulation, act as a signal of cell injury or disease. The body, in response to alarmins released from injured tissue, initiates a repair cascade that directs healing factors to the source of the signal, i.e., the injured tissue. The signal focuses and enhances the speed and intensity of the body's repair response to injury, resulting in accelerated healing. In particular, alarmins signal the mobilization and recruitment of progenitor or stem cells, for example, endothelial progenitor cells, to the site of the injured tissue.

Activation of alarmins requires that the alarmins' cysteines remain free (protonated) to maintain protein folding (and recognition by cognate receptors). Alarmins are inactivated when their cysteines are oxidized to form disulfide bonds. Further, the extracellular space of tissues undergoing highly inflammatory responses contains high amounts of free thiols, whereas those tissues undergoing less inflammatory responses contain smaller amounts of free thiols. Free thiols promote a reducing environment. Accordingly, in tissues that contain high amounts of free thiols, i.e., tissues which undergo highly inflammatory responses, alarmins are likely to be activated in the reducing environment.

The intracellular cytosol and the extracellular milieu are very different environments. The cytosol is highly reducing due to several thiol-regulating enzymatic systems, including the thioredoxin-thioredoxin reductase and glutaredoxin-GSH systems. The extracellular space is normally oxidized due to oxidizing agents including oxygen itself. In an intracellular environment, non-protein thiols, including GSH and cysteine, are most often found in a reduced state. Whereas, in an extracellular environment, non-protein thiols are most often found in the disulfide bond or oxidized form. The reduced or oxidized form of proteins thus depends on the compartments where they are found, e.g., extracellular or intracellular, and, when intracellular, cytosolic or within the endoplasmic reticulum. Cytoplasmic protein cysteine residues typically have free sulfhydryl groups, located in binding pockets of substrates, coenzymes, or metal cofactors, and take part directly in catalytic reactions. The cysteine residues are inactivated by oxidation and remain reduced in the presence of thiol-regulating systems.

Endogenous alarmins modulate the nature and magnitude of cellular injury to the host in addition to mobilizing host repair mechanisms. Alarmins are usually found in the cytosol and, when released into the extracellular space, trigger significant host responses. Host responses, for example, include activating endothelial cells and recruiting inflammatory cells, which promote wound healing and associated stromagenesis, angiogenesis, epithelial proliferation, and modulation of the immune response.

Alarmins trigger numerous wound healing events upon their release into the extracellular space. For example, the release of alarmins into the extracellular space leads to a dose-dependent increase in the expression of intercellular adhesion molecule-1, vascular cell adhesion molecule, and RAGE and increased secretion of TNF-a, IL-8, monocyte chemotactic protein-1, plasminogen activator inhibitor 1, and tissue plasminogen activator. Through polygamous receptors, including RAGE, TLR2, and TLR4, alarmins signal upregulation of adhesion molecules in human endothelial cells, resulting in increased neutrophil recruitment. Extracellular alarmins also act as chemoattractants, leading to mesangioblast stem cell migration to injured tissues. Similarly, chronic alarmin delivery to normal muscle promotes endothelial cell permeability, proliferation, and angiogenesis. Primitive mesangioblasts and bone marrow-derived stem cells injected into mice preferentially migrate to sites of alarmin delivery. Alarmins from necrotic cells lead to increased angiogenesis through endothelial cell sprouting. In the setting of acute injury, alarmins play a role along with coordinate oxidative mechanisms to upregulate and drive TLR signaling. Together, these observations suggest that the earliest events in response to necrotic death drive developments of pro-oxidant mechanisms designed to clear debris and drive the wound-healing process.

An alarmin activator is any substance capable of inducing or maintaining activity of an alarmin. For example, certain alarmins are active when their cysteine residues are free, to maintain protein folding and recognition by cognate receptors, rather than oxidized to form intramolecular or intermolecular disulfide bonds. Accordingly, certain reducing agents act as alarmin activators by protonating or maintaining protonation of cysteine residues in extracellular alarmin molecules present in the tissue microenvironment.

A need exists for a method of adhering or bonding an alarmin or an alarmin activator to a septal closure device or occluder that can provide complete closure of an intracardiac defect, and that is simple and inexpensive to manufacture.

SUMMARY OF THE INVENTION

The invention is directed to cardiovascular occluders and methods of manufacturing the same. Occluders according to the invention have a frame and are coated or bound with an alarmin or an alarmin activator to encourage cardiac tissue growth, such that the patient's own cells (host cells) completely cover the implant and close a cardiac defect, such as a patent foramen ovale (PFO). Accordingly, the invention discloses methods to enhance host cell attachment to and tissue growth over a cardiovascular occluder, although such methods can be used with any implanted medical device such as, but not limited to, a device made of bioabsorbable material.

According to one aspect, the invention is a method for restoring normal anatomic conformation of the cardiac septum in a patient having a congenital intracardiac septal defect. The method includes providing a cardiovascular occluder coated with an alarmin or an alarmin activator, delivering said intracardiac occluder via a percutaneous transvascular route into the right atrium of the patient, introducing said intracardiac occluder into the patient's congenital intracardiac defect, and applying said alarmin or alarmin activator coated cardiovascular occluder to non-injured tissue in the region of the intracardiac defect.

According to another aspect, the invention is a device for treating a cardiovascular abnormality. For example, in one embodiment, the occluder having a frame and an alarmin or an alarmin activator bound to a surface of the occluder. In additional embodiments, the occluder further has a scaffold and the scaffold can be a bioabsorbable polymer, biological material, bioengineered material, or other biocompatible material.

In accordance with another embodiment, the invention can be applied to an environment that does not contain a wound. For example, a PFO environment may not present characteristics of a wound in that a PFO is not a break in tissue that caused by cutting or trauma. However, the present invention contemplates the use of alarmin and alarmin activators as part of the occluder that is used to close a PFO. The inventors believe that the use of a alarmin or alarmin activators in the context of treating tissue in a non-wound environment can promote the healing process in a significant—and unexpected—way. Of course, one specific material disclosed in this application for the above application is uric acid.

In further embodiments of the invention, the alarmin is a damage associated molecular pattern molecule (DAMP), a pathogen associated molecular pattern molecule (PAMP), a nuclear protein HMGB1, an S100 molecule, a heat shock protein, ATP, AMP, adenosine, hypoxanthine, xanthine, inosine, adenosine or uric acid. According to additional embodiments of the invention, the alarmin activator is dithiothreitol, 2-mercaptoethanol, N-acetyl-cysteine, sodium sulfite, glutathione, Probucol™ (2,6-ditert-butyl-4-[2-(3,5-ditert-butyl-4-hydroxyphenyl)sulfanylpropan-2-ylsulfanyl] phenol), ascorbic acid, sodium hypophosphite and sodium borohydride. In further embodiments, the alarmin activator is a gene or drug capable of stimulating endogenous alarmin production.

According to various embodiments of the invention, the occluder is a septal defect occluder for use in septal defects such as a patent foramen ovale, atrial septal defects, ventricular septal defects, patent ductus arteriosis, and ischemic myocardium.

According to another aspect, the invention is a method of treating a septal defect. This method includes providing a cardiovascular occluder comprising a frame and an alarmin or an alarmin activator bound to a surface of the occluder and delivering the cardiovascular occluder to the septal defect.

According to another aspect, the invention is a method of treating an acute myocardial infarct. The method includes providing a cardiovascular occluder comprising a frame and an alarmin or an alarmin activator bound to a surface of the occluder and delivering the cardiovascular occluder to the site of acute infarct in the myocardium.

According to a further aspect, the invention is a method of treating a transient ischemic necrosis of the brain. The method includes providing a cardiovascular occluder comprising a frame and an alarmin or an alarmin activator bound to a surface of the occluder and delivering the cardiovascular occluder to a septal defect in the heart.

According to another aspect, the invention is a method of manufacturing a cardiovascular occluder for treating a cardiovascular abnormality. The method includes forming a cardiovascular occluder frame and binding an alarmin or an alarmin activator to a surface of the occluder.

According to another aspect, the invention is a device for treating a cardiovascular abnormality. For example, in one embodiment, the occluder having a frame and uric acid or a uric acid precursor bound to a surface of the occluder. In additional embodiments, the occluder further has a scaffold and the scaffold can be a bioabsorbable polymer, biological material, bioengineered material, or other biocompatible material.

In further embodiments of the invention, the uric acid precursor is an ATP catabolite, such as hypoxanthine, xanthine, inosine and adenosine. The uric acid precursor can also be a gene or drug capable of stimulating endogenous uric acid production.

According to various embodiments of the invention, the occluder is a septal defect occluder for use in septal defects such as a patent foramen ovale, atrial septal defects, ventricular septal defects, patent ductus arteriosis, and ischemic myocardium.

According to another aspect, the invention is a method of treating a septal defect. This method includes providing a cardiovascular occluder comprising a frame and uric acid or a uric acid precursor bound to a surface of the occluder and delivering the cardiovascular occluder to the septal defect.

According to another aspect, the invention is a method of treating an acute myocardial infarct. The method includes providing a cardiovascular occluder comprising a frame and uric acid or a uric acid precursor bound to a surface of the occluder and delivering the cardiovascular occluder to the site of acute infarct in the myocardium.

According to a further aspect, the invention is a method of treating a transient ischemic necrosis of the brain. The method includes providing a cardiovascular occluder comprising a frame and uric acid or a uric acid precursor bound to a surface of the occluder and delivering the cardiovascular occluder to a septal defect in the heart.

According to another aspect, the invention is a method of manufacturing a cardiovascular occluder for treating a cardiovascular abnormality. The method includes forming a cardiovascular occluder frame and binding uric acid or a uric acid precursor to a surface of the occluder.

The invention is directed to methods of manufacturing cardiovascular occluders incorporating an alarmin with or without an alarmin activator. Occluders according to the invention have an occluder frame and a tissue scaffold. Occluders are formed from, coated with or bound with a polymer incorporating an alarmin with or without an alarmin activator. The incorporated alarmin or alarmin activator encourages cardiac tissue growth, such that the patient's own cells (host cells) completely cover the implant and close a cardiac defect, such as a patent foramen ovale (PFO). Accordingly, the invention discloses methods to incorporate or adhere an alarmin with or without an alarmin activator to a cardiovascular occluder, although such methods can be used with any implanted medical device such as, but not limited to, a device made of bioabsorbable material.

In one aspect, the invention is a method for applying an alarmin with or without an alarmin activator to a cardiovascular occluder. This method comprises the steps of providing a cardiovascular occluder, providing an alarmin solution comprising an alarmin with or without an alarmin activator and a solvent, adding the alarmin solution to a polymer to form a mixture, and coating the occluder with the mixture.

According to various embodiments, the coating step according to the method comprises dip coating, spray coating, and print coating.

In another aspect, the invention is a method for manufacturing a cardiovascular occluder comprising an alarmin with or without an alarmin activator. This method comprises the steps of providing an alarmin solution comprising an alarmin with or without an alarmin activator and a solvent, adding the alarmin solution to a polymer solution to form a mixture, and forming the occluder from the mixture.

According to various embodiments, the occluder further comprises a tissue scaffold. The forming step, according to the method, can be porous film casting, melt blowing, leaching solvent film casting, or double emulsion Film casting. The scaffold can comprise a bioabsorbable polymer, biological material, bioengineered material, or other biocompatible material.

According to additional embodiments, the alarmin is selected from the group consisting of a damage associated molecular pattern molecule (DAMP), a pathogen associated molecular pattern molecule (PAMP), a nuclear protein HMGB1, an S100 molecule, a heat shock protein, ATP, AMP, adenosine, hypoxanthine, xanthine, inosine, adenosine and uric acid, for example.

According to further embodiments, the alarmin activator is a reducing agent selected from the group consisting of dithiothreitol, 2-mercaptoethanol, N-acetyl-cysteine, sodium sulfite, glutathione, Probucol™ (2,6-ditert-butyl-4-[2-(3,5-ditert-butyl-4-hydroxyphenyl)sulfanylpropan-2-ylsulfanyl] phenol), ascorbic acid, sodium hypophosphite and sodium borohydride, for example. The alarmin activator can further comprise a gene or drug capable of stimulating endogenous alarmin production, for example.

According to various embodiments, the cardiovascular occluder is an occluder for repairing a septal defect such as a patent foramen ovale, an atrial septal defect, a ventricular septal defect, and patent ductus arteriosis, for example.

BRIEF DESCRIPTION OF THE FIGURES

FIG. 1 is a perspective view of an intracardiac occluder delivered to an anatomical site in the body of a patient.

DETAILED DESCRIPTION

The current invention provides devices for delivering exogenous alarmins or alarmin activators to a site in a body to trigger the body's endogenous mechanism for repair of injured or abnormal tissue. For example, the body's mechanism for salvaging and restoring injured or diseased tissue may be triggered. Alternatively, the body's mechanism for repair of abnormal tissue may be directed according to the devices and methods of the invention to treat a tissue that is abnormal, such as congenital defects, where the pathogenesis of the abnormal tissue is not related to inflammation, ischemia, infection, or other tissue injury or disease, for example, to restore normal anatomic conformation to a congenital defect. Accordingly, administration of the device containing an alarmin or an alarmin activator increases recruitment of stem cells, endothelial progenitor cells and other healing factors to repair congenital tissue defects in the recipient.

As used in this application, the term defect means a flaw or imperfection. Wound, in contrast, is an injury to the tissue is caused by cutting or tearing. A wound could be created intentionally as in surgery or by unintentional trauma. A defect could be a flaw or imperfection present at birth, such as a congenital defect. A defect could exist with or without a wound.

The current invention provides devices and methods for the controlled delivery and release of one or a combination of more than one alarmin(s) or alarmin activator(s). For the purposes of this invention, an alarmin is any substance capable of inducing or enhancing a tissue healing response in a recipient. Exemplary alarmins include members of the family of damage associated molecular pattern molecules (DAMPs) and members of the family of pathogen associated molecular pattern molecules (PAMPs). Exemplary alarmins further include the nuclear protein HMGB1, the S100 family of molecules (cytosolic calcium-binding proteins), heat shock proteins, interleukins (including IL-1a), HDGF (hepatoma-derived growth factor, Gal1 (Galectin 1) and the purinergic metabolites of ATP, AMP, adenosine and uric acid.

According to one embodiment of the invention, the alarmin is uric acid or a uric acid precursor. Uric acid is the common name for 7,9-dihydro-1H-purine-2,6,8(3H)-trione or 2,6,8 trioxypurine. The embodiment further contemplates the use of the urate ion and salts of uric acid, including but not limited to sodium urate, ammonium urate, lithium urate and potassium urate. Uric acid precursors include, for example, uric acid metabolite(s), gene(s), gene fragment(s), protein(s), protein fragment(s), and pharmaceutical composition(s) that are, for example, (i) metabolized by the body to uric acid or (ii) stimulate the endogenous production of uric acid. Uric acid metabolites include, for example, ATP catabolites such as adenosine, hypoxanthine, xanthine and inosine.

Alarmin activators include small molecules necessary for maintaining the activity of administered and/or endogenous alarmins. Exemplary alarmin activators include thiol containing reducing agents, including, but not limited to, dithiothreitol, 2-mercaptoethanol, N-acetyl-cysteine, sodium sulfite, glutathione, and Probucol™ (2,6-ditert-butyl-4-[2-(3,5-ditert-tbutyl-4-hydroxyphenyl)sulfanylpropan-2-ylsulfanyl]phenol). Exemplary alarmin activators further include non-thiol reducing agents, including, but not limited to, ascorbic acid, sodium hypophosphite, and sodium borohydride.

According to one embodiment, a combination of at least one alarmin and at least one alarmin activator are co-administered. The combination of an alarmin and an alarmin activator works synergistically to facilitate inflammation and healing. According to an additional embodiment, the cardiovascular device is coated with multiple layers of two or more alarmin(s) or alarmin activator(s). For example, an outer coating layer can comprise an alarmin, e.g., uric acid, producing an initial alarmin burst, and an inner coating layer can comprise an alarmin activator, e.g., a thiol containing reducing agent, to sustain the initial alarmin response. As the body responds to the initial bolus of alarmin, infiltrating inflammatory cells and the local endothelium release additional alarmins which should have prolonged activity in the presence of elevated co-administered or later administered alarmin activators.

According to one embodiment of the invention, one or more alarmin(s) or alarmin activator(s), or a combination of alarmin(s) and alarmin activator(s) is coated or bonded to the surface of a cardiovascular device, e.g., an occluder for implantation at or adjacent a cardiovascular abnormality such as a congenital septal defect or ischemic myocardial tissue. Congenital septal defects include, for example, atrial septal defects, ventricular septal defects, patent foramen ovale and patent ductus arteriosis.

While the congenital septal defects are considered abnormal because they are holes or shunts between the right and left ventricles of the heart, such as atrial septal defects and ventricular septal defects, the cells and the tissues of the septa are not injured or diseased and, therefore, do not produce signals capable of initiating a tissue repair response. Applicant has made the seminal and surprising discovery that administration of an alarmin, an alarmin activator, or a combination of the two to such septal defect according to the invention results in the production of a localized signal in the region of the non-injured tissue of the defect to recruit progenitor cells, stem cells, endothelial cells, inflammatory cells and other repair mediators to the cardiac tissues in the region of the defect. Moreover, applicant has discovered that the endogenous cells surrounding the defect may migrate and attach to non-injured tissue in the area undergoing treatment to induce cellularization and closure of the cardiac defect. Cells that may be induced to migrate and attach include but are not limited to fibroblasts, myocytes, endothelial cells and their progenitors, and progenitor cells of the circulating blood.

In general, referring to FIG. 1, a typical cardiovascular occluder 10 includes a frame having a proximal occlusion shell 12 and an opposite distal occlusion shell 14. According to the illustrative embodiment, the distal occlusion shell 14 is released into the chamber 22 and the proximal occlusion shell 12 is released into the chamber 20 to cover the intracardiac defect 24.

According to one embodiment, the frame can further include a scaffold material attached to the frame. The frame apposes the cardiac septum and provides support to the scaffold material, thereby occluding an intracardiac defect, for example, a patent foramen ovale (PFO). The scaffold material covers the defect and provides surface area for host cell migration and attachment to and tissue growth into the site of the defect, thereby encouraging anatomical closure of the defect.

According to the invention, the closure of a defect, e.g., a patent foramen ovale can be improved by modifying the cardiovascular occluder to deliver at least one alarmin, alarmin activator, or a combination of alarmin(s) and alarmin activator(s) to the intracardiac tissue to be treated to accelerate recruitment of endogenous cells, for example, fibroblasts, myocytes, endothelial cells and their progenitors, and progenitor cells of the circulating blood, formation of granulation tissue and re-endothelialization (i.e., healing and cell migration and tissue growth) at the site of the intracardiac defect.

In one embodiment, the frame can be formed of any biocompatible metal or polymer, bioabsorbable polymer, or a shape memory polymer. In another embodiment, the tissue scaffold can be formed of any flexible, biocompatible material capable of promoting host tissue growth including, but not limited to, polyester fabrics, Teflon-based materials, such as ePTFE, polyurethanes, metallic materials, polyvinyl alcohol (PVA), extracellular matrix (ECM) isolated from a mammalian tissue, or other bioengineered materials, bioabsorbable polymers, or other natural materials (e.g., collagen), or combinations of these materials. Furthermore, the surface of the tissue scaffold can be modified with biological, pharmaceutical and other active ingredients such as anti-coagulants, anti-thrombogenic agents, cells, growth factors or drugs to improve defect healing and/or to prevent blood clotting. The scaffold can be attached to a cardiovascular occluder frame or to another scaffold by sutures, heat treatment, adhesives, or any other chemical bonding process.

Exemplary bioabsorbable polymers for use in making cardiovascular occluder frames and/or scaffolds include polyhydroxyalkanoates, for example poly-4-hydroxybutyrate (P4HB). Such materials are strong and flexible, but also bioabsorbable. Accordingly, it is necessary to ensure that sufficient host tissue ingrowth to close the defect occurs at the implantation site prior to complete absorption of the device.

According to one embodiment of the invention, the device can be formed of a material incorporating a substance that encourages cell recruitment, cell attachment and tissue growth. According to one embodiment of the invention, the surface of the device can be coated with or bonded to a substance that encourages cell recruitment, cell attachment and tissue growth. For instance, in one embodiment, the scaffold and/or frame is coated with at least one alarmin, alarmin activator, or a combination of alarmin(s) and alarmin activator(s).

According to one exemplary method of manufacturing the cardiovascular occluder, the occluder frame and/or scaffold is dipped into or spray coated with a solution of an alarmin or an alarmin activator, for example, uric acid. Uric acid and uric acid precursors are available commercially (e.g., from Sigma-Aldrich Co., St. Louis, Mo., USA).

Alarmin with or without alarmin activator can be applied to the surface of a medical implant through a simple dip coating process. For example, to coat a biocompatible scaffold or frame with uric acid according to the invention, a 50 microgram/microliter solution of uric acid is made by dissolving uric acid crystals in sterile sodium chloride solution to 0.9% wt/vol. The scaffold or frame is then cleaned with ethyl alcohol and deionized water prior to being soaked in the uric acid solution for 15 minutes. The scaffold or frame is dried for approximately one to four hours between coats. A plurality of coats of uric acid may be applied. Alternatively, the uric acid solution above can be sprayed onto the frame and/or scaffold of the occluder. A plurality of uric acid coats may be applied.

The frame and/or tissue scaffold of the occluder can be coated with or bonded with an alarmin with or without an alarmin activator according to the following exemplary methods. According to one exemplary method, the alarmin with or without an alarmin activator is added to a solvent to form an alarmin solution. The alarmin solution is combined with a polymer melt or a polymer solution to form a mixture. The resulting mixture is in liquid form for simple and inexpensive application to the surface of the frame and/or scaffold of the occluder according to the following exemplary methods.

In an exemplary polymer solution comprises a solvent, for example 1-methyl-2-pyrrolidiinone at a concentration of about 60-80% by weight (about 20 mg), and a polymer material, for example polyhydroxyalkanoate (PHA) at a concentration of about 20-40% by weight (about 6 mg) (additional specific polymers are also contemplated, for example, poly-4-hydroxybutyrate (P4BP)). According to a further exemplary embodiment, the polymer solution further includes a radiopaque substance (for example, tungsten at a concentration of about 60-70% by weight (about 40 mg)). The uric acid solution is then combined with a polymer melt or a polymer solution to form a mixture. The frame and/or tissue scaffold is cleaned with ethyl alcohol and deionized water for 15 minutes prior to administration of the mixture.

According to another exemplary method, a polymer solution comprises a solvent and a polymer material dissolved in the solvent. According to another embodiment, a polymer melt comprises a polymer that is melted by heat or other energy source. According to another embodiment of the invention, following preparation of the polymer solution or polymer melt, the polymer solution or polymer melt is combined with a solid form of an alarmin with or without an alarmin activator to form an emulsion or suspension. The resulting emulsion or suspension is for simple and inexpensive application to the surface of the frame and/or tissue scaffold of the occluder according to the following exemplary methods.

According to one embodiment of the invention, following application of the mixture, emulsion or suspension to the surface of the occluder, the solvents that dissolve the polymer and/or alarmin with or without alarmin activator evaporate, resulting in the formation on the surface of the occluder of a solid or porous solid layer of the polymer material incorporated with alarmin with or without alarmin activator. According to a preferred embodiment, a polymer-based occluder frame and/or tissue scaffold comprises the same polymer material as the polymer contained within the mixture, emulsion or suspension, resulting in improved adherence or bonding of the mixture, emulsion or suspension to the polymer frame and/or scaffold.

Preferred methods of fabricating the frame and/or tissue scaffold of a polymer occluder from polymer materials include solvent casting, melt processing, extrusion, injection and compression molding, and spray drying. Polymers for use according to the described methods are preferably prepared directly from a fermentation based process, or by a solvent evaporation technique, double emulsion technique, or by microfluidization, using methods available in the art. (Koosha, F. Ph. D. Dissertation, 1989, Univ. Nottingham, UK., Diss. Abstr. Int. B 51:1206 (1990); Bruhn, B. W. and Mueller, B. W. Proceed. Intern. Symp. Control. Rel. Bioact. Mater. 18:668-69 (1991); Conti, B. et al., J. Microencapsulation, 9:153-166 (1992); Ogawa, Y. et al., Chem. Pharm. Bull., 36:1095-103 (1988); Mathiowitz, E. and Langer, R. "Polyanhydride microspheres as drug delivery systems," M. Donbrow Ed., in "Microcapsules Nanopart. Med. Pharm." CRC, Boca Raton, Fla., 1992, Ch. 5, pp. 99-123.)

The invention further provides a method of treating cardiovascular abnormalities by providing a cardiovascular occluder with uric acid to the site of the abnormality. According to one embodiment, the abnormality is a congenital septal defect formed of otherwise non-injured tissues and the occluder is delivered to the septal defect. According to another embodiment, the abnormality is an acute myocardial infarct and the occluder is delivered to the site of acute infarct in the myocardium. In a further embodiment, the abnormality is a transient ischemic necrosis of the brain or migraine. The occluder according to the invention is delivered to the septal defect in the patient's heart to occlude the defect and thereby prevent release of defect-associated thrombi from release into the patient's circulation.

Example

Implantation of Band With Uric Acid

In the presently concluded study, six small animals were used. The local tissue response to a septal repair implant component augmented with uric acid and implanted in muscle tissue for four weeks was evaluated. In this study, four treatment groups were investigated along with a negative control group, high density polyethylene. The four groups were an uncoated septal repair component, a septal repair component with 0% uric acid bands, a septal repair component with 10% uric acid bands and a septal repair component with 20% uric acid bands.

The uric acid bands were printed on tubular septal repair components using a computerized, motion controlled stage with a motionless pattern generating device. The printed material was a mixture of poly-4-hydroxybutyrate, uric acid crystals and 1-methyl-2-pyrrolidinone. The cured bands consisted of 0, 10 or 20% uric acid crystals in poly-4-hydroxbutyrate. The surface coverage of these bands was greater than 75% of the component surface area.

The test samples were implanted into the paravertebral muscles of New Zealand White rabbits of at least 2.5 kg. After 4 weeks postimplantation, the test sample sites were evaluated under low magnification for capsule formation and evidence of irritation. Sections of each test article were prepared for histological evaluation. Microscopic evaluations for inflammation, fibrosis, hemorrhage, traumatic necrosis, mineralization and particulate debris were completed.

A summary of the microscopic results is shown in Table 1. Each sample was tested in two locations in six different animals. The scores presented in Table 1 are a sum of the averages for each animal. The minimal possible score is 0 and the maximum is 24.

TABLE 1

Table 1. Uric Acid Banded Septal Repair Component Tissue Response Summary

|  | 20% Uric Acid | 10% Uric Acid | 0% Uric Acid | No Band | Control |
|---|---|---|---|---|---|
| Lymphocytes | 5 | 8 | 4 | 4 | 3 |
| Fibrosis | 7 | 7 | 6 | 6 | 6 |

As expected, the groups with either no bands or bands with 0% uric acid elicited a tissue response similar to the negative control with the exception of an increase in lymphocytes. Those groups with uric acid bands demonstrated a further increase in lymphocytes in additional to an increase in fibrosis. A previous study (Shi, Y., J. E. Evans, and K. L. Rock, *Molecular identification of a danger signal that alerts the immune system to dying cells*. Nature, 2003. 425 (6957): p. 516-21) showed uric acid stimulates $CD8^+$ T cells, one type of lymphocytes. Therefore, the increase in lymphocytes was expected. Unexpectedly, this increase in lymphocytes corresponded to an increase in fibrosis which indicates that uric acid has the potential to stimulate tissue generation along with its previously known function as a danger signal or "alarmin".

In order to implant the samples into the test subjects an injury (however minor) to the surrounding muscle tissue was unavoidable. Because uric acid is released through tissue injury, the effect of uric acid in the groups with uric acid marker bands may be partially masked by the native uric acid released in all groups by the tissue injury. One skilled in the art will recognize the limitations presented by the unavoidable injury and the significance of the testing data as demonstrating a superior response. Accordingly, the small increase in lymphocytes and fibrosis shown in the uric acid groups in this study is expected to be more profound when translated to repairing atrial septal defects in which little to no tissue injury occurs during implant placement.

Example

Implantation of A Uric Acid Occluder In A Human

A cardiovascular occluder having a frame and uric acid or a uric acid precursor bound to the occluder according to any one of the methods described herein could be implanted in a human. The cardiovascular occluder will be implanted at a cardiovascular abnormality, such as a patent foramen ovale or atrial septal defect via a percutaneous transvascular procedure using a catheter. Such implantation procedures are well known in the art. At 30 days, significant cell proliferation and tissue growth would be expected to occur. By 90 days the occluder is expected to completely encapsulate with host tissue. By 1 year, the defect is expected to completely closed with host tissue.

While this example is specifically focused on human implantation, such a device is contemplated for implantation in a variety of mammals such as, for example, a dog, a cat, a horse, a cow, or a pig.

The current invention provides methods for manufacturing medical implants for delivering exogenous alarmins with or without alarmin activators to a site in a body to trigger the body's endogenous mechanism for repair of injured or abnormal tissue. Administration of the medical implant manufactured according to the disclosed methods and containing an alarmin with or without an alarmin activator increases recruitment of stem cells, endothelial progenitor cells and other healing factors to repair congenital tissue defects in the recipient.

According to one embodiment of the invention, one or more alarmin(s) or alarmin activator(s), or a combination of alarmin(s) and alarmin activator(s) is incorporated into, or coated or bonded onto the surface of a cardiovascular device, e.g., an occluder for implantation at or adjacent a cardiovascular abnormality such as a congenital septal defect or ischemic myocardial tissue. Congenital septal defects include, for example, atrial septal defects, ventricular septal defects, patent foramen ovale and patent ductus arteriosis. While the congenital septal defects are considered abnormal because they are holes or shunts between the right and left atrium and ventricle of the heart, the cells and the tissues of the septa are not injured or diseased and, therefore, do not produce signals capable of initiating a tissue repair response.

Dosage: To evaluate the inflammatory response to different dosages of alarmin with or without alarmin activators and to determine an optimum dose of alarmin with or without alarmin activator per occluder, a dosage study will be performed in rabbits. According to an exemplary investigatory procedure, using standard animal investigation techniques, a single dose of monosodium urate will be administered to muscle tissue in rabbits. Doses ranging from 0 mg to 200 mg will be investigated. Four weeks following administration, the treated tissue will be investigated for the presence of inflammatory molecules and progenitor cell infiltration. It is expected that a dose of between 0 mg and 200 mg per occluder will be optimal for healing.

Dip Coating: According to one exemplary method, the administration of the mixture to the frame and/or tissue scaffold of the cardiovascular occluder is a dip coating process. According to this method, uric acid solution is prepared according to the steps disclosed above. The uric acid solution is then added to a polymer melt or solution to form a mixture. The occluder frame and/or tissue scaffold, after been cleaned with ethyl alcohol and deionized water, is then dipped into the mixture. As the solvent evaporates, the resulting polymer/uric acid coating adheres to or is bonded to the surface of the occluder frame and/or tissue scaffold. According to one embodiment of the invention, one coat is applied to the frame and/or tissue scaffold. According to another embodiment of the invention, a plurality of coats of the mixture may be applied. In the event of multiple coating, the frame and/or tissue scaffold is dried for approximately one to four hours between coats.

Spray Coating: According to another exemplary method, the frame and/or tissue scaffold of the occluder is spray coated with a mixture of uric acid solution and polymer melt or solution. According to this method, a mixture of the uric acid solution and/or polymer melt or solution is prepared according to the methods described above. The frame and/or tissue scaffold of the occluder is then sprayed with a coating of the mixture. As the solvent evaporates, the resulting polymer/uric acid coating adheres to or is bonded to the surface of the occluder frame and/or scaffold. According to one embodiment of the invention, one coat is applied to the frame and/or tissue scaffold. According to another embodiment of the invention, a plurality of coats of the mixture may be applied. In the event of multiple coating, the frame and/or scaffold is dried for approximately one to four hours between coats.

Print Coating: According to another exemplary method, the frame and/or tissue scaffold of the occluder is printed with a mixture of uric acid solution and polymer melt or solution. According to one exemplary method, a mixture of the uric acid solution and/or polymer melt or solution is prepared according to the methods described above. The frame and/or tissue scaffold of the occluder is then printed with a coating of the mixture using, for example, ink jet printing techniques known to one of skill in the art. As the solvent evaporates, the resulting polymer/uric acid coating adheres to or is bonded to the surface of the occluder frame and/or scaffold. According to one embodiment of the invention, one coat is applied to the frame and/or tissue scaffold. Anther to another embodiment of the invention, a plurality of coats of the mixture may be applied. In the event of multiple coating, the frame and/or scaffold is dried for approximately one to four hours between coats.

The frame and/or tissue scaffold of the occluder can be formed from a polymer material incorporating an alarmin with or without an alarmin activator using a wide range of polymer processing techniques. Preferred methods of fabricating polymer-based occluder frames include extrusion, injection molding, laminating, rolling, or other melt processing methods known to those skilled in the art. It is desirable to utilize a porous material for many tissue engineering applications. There are several advantages to using a porous material such as better diffusion of fluids and nutrients, increased surface area, increased cellular attachment, faster degradation, and greater tissue contact. For many tissue engineering applications, it is desired to utilize pores which are approximately 50 to 200 um in diameter (for incorporation of cells, preferred interstitial spacings on the order of 100 to 300 microns are not unusual), however, the optimum porosity, pore size and density of a porous material will vary depending upon its intended application. Pores can be introduced in a polymeric material using a variety of techniques such as foaming agents, processing of fibers into woven or non-woven structures, phase separation and leaching. Preferred methods of fabricating polymer based occluders tissue scaffold include solvent casting, melt processing, fiber processing/spinning/weaving, extrusion, injection and compression molding, lamination, and solvent leaching/solvent casting. Such methods of fabricating polymers into occluder frames or scaffolds are known to those skilled in the art.

Another preferred method involves melting or solvent processing a suitable polymer into an appropriate mold and perforating the molded material using a laser or other means to achieve the desired porosity. Also preferred are methods that include rolling a compression molded polymer sheet into a loop and heat sealing. The polymer sheet optionally may be rolled with another material, such as a second biodegradable polymer. For example, the latter material could be a non-woven material of polyglycolic acid, polylactic acid, or a copolymer of glycolic and lactic acids. Such a procedure will provide a laminated tube suitable for use in the engineering of various body parts, e.g., parts to occlude defects in the heart.

Melt Blown: Melt blowing is a process for producing fibrous webs or articles directly from polymers or resins using high-velocity air or another appropriate force to attenuate the filaments. According to one exemplary method, the occluder tissue scaffold is melt blown from a mixture of a polymer material incorporating an alarmin with or without an alarmin activator, for example, uric acid. According to this method, the polymer is melted by a thermal processor, for example an extruder, at an appropriate temperature. A uric acid solution is prepared according to the methods described above. The uric acid solution is added to the polymer melt to form a mixture. As soon as the mixture is extruded from the die holes, high velocity hot air streams attenuate the polymer streams to form microfibers. The hot air stream containing the microfibers progresses toward the collector screen to form a self-bonded nonwoven web, for example an occluder tissue scaffold. The fibers are generally laid randomly (and also highly entangled) because of the turbulence in the air stream. In an alternative embodiment, an alarmin with or without an alarmin activator in solid form is added to the polymer melt. In another embodiment, both polymer and alarmin with or without an alarmin activator in solid form are processed through a thermal processor, such as an extruder, to form a molten mixture.

Leaching Solvent Cast Film: According to another exemplary method, a cardiovascular occluder tissue scaffold is formed through a leaching solvent casting process from a mixture of a polymer solution and an alarmin solution including an alarmin with or without an alarmin activator. According to an exemplary method, the alarmin solution is a uric acid solution prepared according to the methods disclosed above. A polymer solution containing leachable materials is also prepared by mixing a solvent and a polymer at an appropriate ratio. The leachable material is chosen such that it is poorly soluble in the polymer and readily removed by leaching. The uric acid solution is then added to the polymer solution to form a mixture. The mixture is formed into the desired shape and then the leachable material selectively dissolved away using a solvent in which the leachable material is soluble but in which the polymer is poorly soluble. The leachable material dissolves away to leave behind vacant pores. The size, distribution, and weight percent of the leachable material particles may be chosen to produce materials with a range of porosities. According to one embodiment, suitable leachable materials are simple non-toxic salts which dissolve readily in aqueous media such as an inorganic or organic material, for example, a salt, sugar, protein, or polymer. The porosity of the membranes may be controlled somewhat by selecting leachable materials with different particle sizes. In an alternative embodiment, an alarmin with or without alarmin activator in solid form is added to the polymer solution. In an alternative embodiment, an alarmin with or without alarmin activator in solid form is added to the polymer solution.

Double Emulsion Solvent Cast Film: According to another exemplary method, the occluder tissue scaffold is formed through a double emulsion solvent casting process from a mixture of a polymer solution and an alarmin solution comprising and alarmin with or without an alarmin activator. According to this method, a polymer is dissolved in a water immiscible solvent to form a polymer solution. Uric acid solution, prepared according to the methods described above, is then added to the polymer solution to form a mixture. Water with incorporated detergent is added to the polymer solution or the mixture to create an emulsion. The emulsion is poured into a mold to a desired thickness. The solvent evaporates, leaving the uric acid embedded in the polymer. The resulting tissue scaffold is then rinsed to remove the detergent and allowed to dry. In an alternative embodiment, an alarmin with or without alarmin activator in solid form is added to the polymer solution or the emulsion.

The invention claimed is:

1. A cardiovascular occluder for treating a cardiovascular abnormality by deployment in a subject's heart, the occluder comprising a frame and an alarmin bound to a surface of the occluder, wherein the occluder provides controlled release of the alarmin to the cardiovascular abnormality and promotes fibrosis within the cardiovascular abnormality, and wherein the alarmin is uric acid.

2. The occluder of claim 1 further comprising a scaffold.

3. The occluder of claim 2 wherein the scaffold comprises a bioabsorbable polymer, biological material, bioengineered material, or other biocompatible material.

4. The occluder of claim 1 wherein the occluder comprises one or more additional alarmins selected from the group consisting of a damage associated molecular pattern molecule (DAMP), a pathogen associated molecular pattern molecule (PAMP), a nuclear protein HMGB1, an S100 molecule, a heat shock protein, ATP, AMP, adenosine, hypoxanthine, xanthine, inosine and adenosine.

5. The occluder of claim 1 wherein the occluder comprises an alarmin activator selected from the group consisting of dithiothreitol, 2-mercaptoethanol, N-acetyl-cysteine, sodium sulfite, glutathione, Probucol.TM. (2,6-ditert-butyl-4-[2-(3,5-ditert-butyl-4-hydroxypheny)sulfanylpropan-2-ylsulfanyl]phenol), ascorbic acid, sodium hypophosphite and sodium borohydride.

6. The occluder of claim 1 wherein the alarmin activator comprises a gene or drug capable of stimulating endogenous alarmin production.

7. The occluder of claim 1 wherein the occluder is a septal defect occluder.

8. The occluder of claim 7 wherein the septal defect is a patent foramen ovale.

9. The occluder of claim 7 wherein the septal defect is an atrial septal defect.

10. The occluder of claim 7 wherein the septal defect is a ventricular septal defect.

11. The occluder of claim 7 wherein the septal defect is patent ductus arteriosis.

12. The occluder of claim 1 wherein the cardiovascular abnormality is ischemic myocardium.

13. A cardiovascular occluder for treating a cardiovascular abnormality by deployment in a subject's heart, the occluder comprising a frame and uric acid, wherein the occluder provides controlled release of the uric acid to the cardiovascular abnormality and promotes fibrosis within the cardiovascular abnormality.

14. The occluder of claim 13 further comprising a scaffold.

15. The occluder of claim 14 wherein the scaffold comprises a bioabsorbable polymer, biological material, bioengineered material, or other biocompatible material.

16. The occluder of claim 13 further comprising an ATP catabolite selected from the group consisting of hypoxanthine, xanthine, inosine and adenosine.

17. The occluder of claim 13 further comprising a gene or drug capable of stimulating endogenous uric acid production.

18. The occluder of claim 13 wherein the occluder is a septal defect occluder.

19. The occluder of claim 18 wherein the septal defect is a patent foramen ovale.

20. The occluder of claim 18 wherein the septal defect, is an atrial septal defect.

21. The occluder of claim 18 wherein the septal defect is a ventricular septal defect.

22. The occluder of claim 18 wherein the septal defect is patent ductus arteriosis.

23. The occluder of claim 13 wherein the cardiovascular abnormality is ischemic myocardium.

* * * * *